(12) United States Patent
Bonaldo

(10) Patent No.: US 7,118,560 B2
(45) Date of Patent: Oct. 10, 2006

(54) NEEDLELESS LUER ACTIVATED MEDICAL CONNECTOR

(75) Inventor: Jean M. Bonaldo, Upland, CA (US)

(73) Assignee: Creative Plastic Technology, LLC, Upland, CA (US)

( * ) Notice: Subject to any disclaimer, the term of this patent is extended or adjusted under 35 U.S.C. 154(b) by 463 days.

(21) Appl. No.: 10/376,886

(22) Filed: Feb. 28, 2003

(65) Prior Publication Data

US 2004/0172006 A1    Sep. 2, 2004

(51) Int. Cl.
*A61M 5/00* (2006.01)
*A61M 25/16* (2006.01)
*A61M 25/18* (2006.01)

(52) U.S. Cl. .................. 604/537; 604/248

(58) Field of Classification Search .......... 604/181, 604/167.04, 167.05, 532, 539, 248, 905, 604/523, 30, 32, 533–537; 251/149; 128/912
See application file for complete search history.

(56) References Cited

FOREIGN PATENT DOCUMENTS

WO     WO 01/93936 A1 * 12/2001

\* cited by examiner

*Primary Examiner*—Nicholas D. Lucchesi
*Assistant Examiner*—Matthew F. DeSanto
(74) *Attorney, Agent, or Firm*—Roth & Goldman, P.A.

(57) ABSTRACT

A medical fluid flowline connector comprised of axially aligned relatively rotatable male and female Luer parts and an axially compressible elastomeric seal therebetween includes an elastomeric stopper in the female Luer, the stopper having a swabbable end urged outwardly of the female Luer. The stopper is guided on an axially extending elongated flow conducting insert which has an end which contacts a deformable slit in the swabbable end of the stopper to ensure deformation and opening of the slot as a male Luer at the end of a fluid flowline is pushed against the stopper. The stopper skirt is deformed and displaced into annular space between the female Luer and the insert, the stopper having bellows like walls which engage the female Luer and insert.

21 Claims, 6 Drawing Sheets

NEEDLELESS LUER ACTIVATED MEDICAL CONNECTOR

BACKGROUND OF THE INVENTION AND PRIOR ART

The present invention relates to connectors for use in medical flow lines for blood transfer, intravenous medication and nutritional supply, and the like. In accord with usual medical terminology, the connector may be referred to as having distal and proximal ends respectively designating the ends of the connector which are ordinarily positioned nearest and farthest from the patient.

U.S. Pat. No. 5,273,533 issued Dec. 28, 1993 and U.S. Pat. No. 5,306,243 issued Apr. 26, 1994 to Bonaldo each disclose a medical connector having an elastomeric element in the form of a septum or fluid barrier disposed in a two part plastic housing. The septum is pierced by a pointed cannula in the connector when making the connection to the fluid flowline. Disconnection of the flow line allows the elastomer to re-seal the connector. Repeated usage of such connectors may cause the connector to leak or become contaminated with particulate material such as particles which may detach from the septum. Current Food and Drug Administration (FDA) requirements dictate that medical flowline connectors not remain connected for more than 24 hours at a time. For this reason, repeated disconnection of the flowlines from the connector and decontamination of the connector and flowlines, as by swabbing with alcohol, is at least a daily occurrence. Thus, these connectors may be actuated or cycled many times and must remain leak free and reliably avoid introduction of contaminants such as cotton fibers from swabs used to clean the connectors into the flowline.

Medical connectors which use resilient flow barriers which are repeatedly pierced during use of the connector become more subject to fluid leakage with increased actuation cycles, particularly if connected in an infusion pump line which may subject the connector to pressures as high as 27 psi. U.S. Pat. No. 5,947,954 issued Sep. 7, 1999 to Bonaldo, the teachings of which are incorporated herein by reference, discloses a needleless connector which is addressed to the above concerns which includes attached relatively rotatable male and female Luer connector parts with an eccentrically positioned flow passageway at the inner end of the female Luer connector. A removable plastic plug, permanently attached to the connector by a strap, and which fulfills the function of a cleansing swab for the female Luer connector is also provided as an optional feature.

Although the removable plug when properly used closes the female Luer when the female Luer is not connected to a flowline, it has been found in practice that additional manipulation of the plug is required for proper use and that the plug can inadvertently become dislodged leaving the female Luer open to atmosphere and possible contamination. Accordingly, a more reliable and easy to use swabbable stopper for the female Luer part of the connector has been developed which always remains in proper position yet which also permits easy connection/disconnection of the male Luer end of a flowline to/from the connector valve is disclosed and claimed in a more recent U.S. Pat. No. 6,364,869 issued Apr. 2, 2002 to Bonaldo, the full teachings of which are also incorporated herein by reference. This stopper has an exterior end which essentially completely closes the otherwise open end of the female Luer when the connector is not in use to prevent introduction of fibers or other contaminants into the flow path in the connector. However, since fluid flow takes place along the outside of a stopper guide post mounted in the connector, it has been found that fluid may remain in the annular space between the post and inside wall of the swabbable stopper.

There remains a need to provide a further improved medical connector which includes a female Luer end having a swabbable elastomeric stopper which still further reduces the likelihood of contaminant entry to the fluid flow path. Also, there remains a need for a connector which has readily observable indicators thereon to enable the user to determine if the relatively rotatable parts of the connector are positioned to place the connector in the open or closed position.

SUMMARY OF THE INVENTION

Disclosed herein is a medical connector having a longitudinal axis and interconnected axially aligned relatively rotatable male and female Luer parts aligned to provide a housing whereby relative rotation of said parts opens and closes a fluid flow path through the connector, the parts being configured for connection to external male and female Luer flowlines. The device includes a fluidic channel insert, also referred to herein as a flow conducting insert, which is non-rotatably supported in the female Luer part. The insert has an internal fluid passageway extending from a first axially aligned end to a second end, said second end being offset from the connector axis. A compressible seal is positioned in the male Luer part and abuts the second end of the insert, the seal having a flow passageway extending between a first axially offset end at the second end of the insert to an axially aligned second end, such that said ends of said flow passageways in abutting ends of the insert and seal may be aligned to open a fluid flow path through the connector. An elastomeric stopper is mounted over the insert, the stopper having a swabbable end providing a deformable normally closed opening which may be opened when the swabbable end of the stopper is pushed over the end of the insert by an external male Luer received in said female Luer part. The stopper has an annular axially collapsible skirt engaged with the female Luer part and insert.

A swabbable stopper having a unique configuration is also disclosed and claimed.

DESCRIPTION OF THE PREFERRED EMBODIMENT

Figure 1:
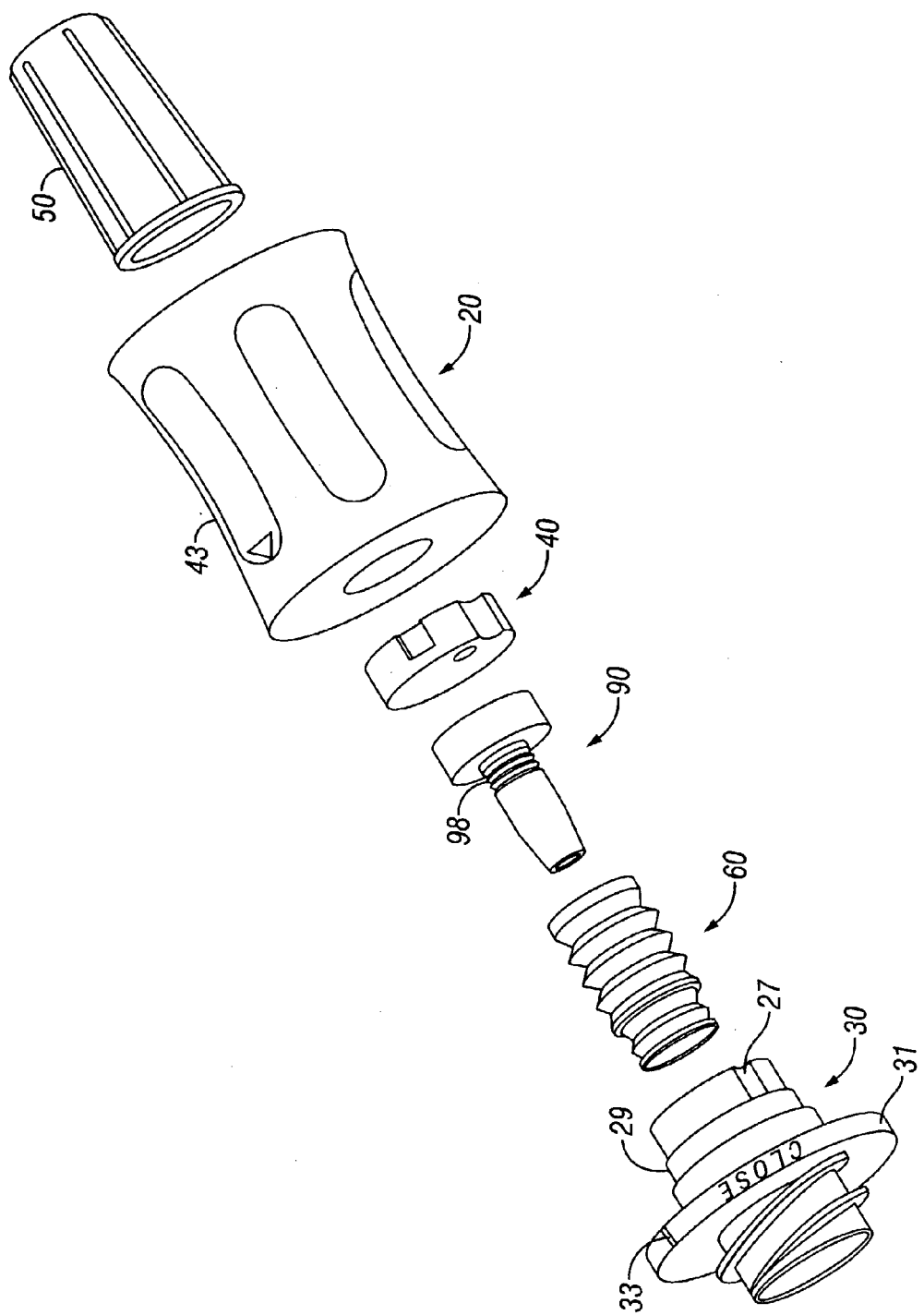
FIG. 1 comprises an exploded perspective view of the presently preferred embodiment of a medical connector according to the present invention including a contamination cap for a male Luer part.

The medical connector 10 in which the present invention is used comprises essentially a five part connector comprising a housing formed by a male Luer configured part 20 connected to a female Luer configured part 30 with a cylindrical resilient seal 40 the outer edges of which are compressed between a seat valve 22 formed at the end wall in the male Luer part 20 and an end wall 32 of the female Luer part 30. The male Luer part 20 and female Luer part 30 are aligned on a common longitudinal axis and are rotatable with respect to each other through an angle of preferably about 180° around the longitudinal axis to activate and deactivate the connector by opening and closing flow passageway through the connector. The female Luer part 30 includes a collar 31 having a face which abuts an end face of the male Luer part 20, preferably along a transverse or radial plane. The collar 31 functions to block ingress of fluid which may be spilled during disconnection of an external male Luer 100 axially between the facing portions of the male and female Luer parts 20, 30 since any spilled fluid ordinarily contacts the left end or side (as viewed in the drawings) of the female Luer 30. The Exteriorly exposed surfaces adjacent the abutting faces are provided with visible or tactile indicia such as arrows 33, 43 which may be aligned by relative rotation of the female and male Luer parts 20, 30 to indicate the activated and deactivated, i.e., the full open and closed positions of the connector.

Figure 6:
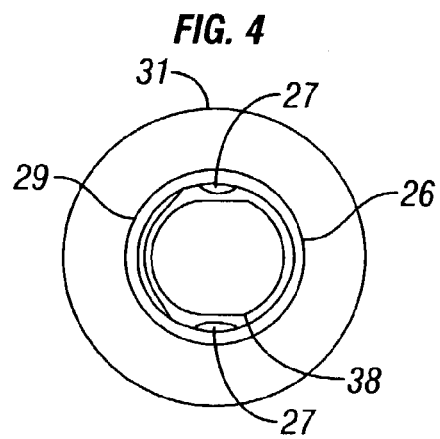
FIG. 6 is a right end view of the female Luer housing part.
Figure 7:
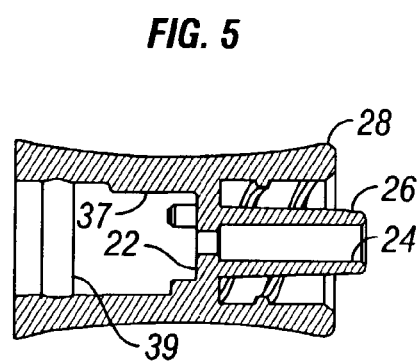
FIG. 7 is a cross-sectional elevation of a male Luer housing part.
Figure 8:
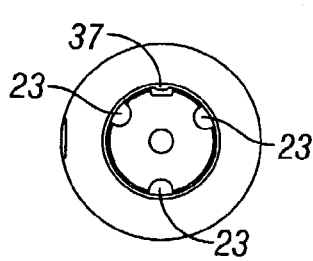
FIG. 8 is a left end view of the male Luer housing part.
Figure 9:
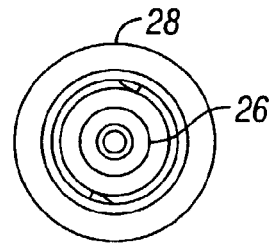
FIG. 9 is a right end view of the male Luer housing part.

A longitudinally extending rib 37 inside the male Luer part 30 slides along a cam surface on the exterior of the right end of the female Luer part 30 and snaps into one of two axially extending cam grooves 27 on the exterior surface of the right end of the female Luer part when the Open and Closed indicia 33, 43 are aligned at the full open and full closed positions of the connector. The grooves 27 and finger 37 are preferably configured as shown in FIGS. 6 and 8 with curved portions bounded by flat generally radially extending sides at the ends of the curved portions to assure proper full open and full closed relative positioning of the parts 20, 30. A concave gripping surface 21 on the male Luer part 20 may include elongated indentations or other roughening to facilitate fingertip gripping of the connector.

As seen in FIGS. 1–3 and 7–9, the male Luer part 20 includes an internal flow passageway 24 in a frusto-conical Luer tapered male extension 26 and an internally threaded skirt 28 for connection to an external female slip or lock Luer in a flowline. The female Luer part 30 has an internal frusto-conical Luer taper at its left end as seen in the drawings and is also configured as a lock Luer externally threaded at 34; however, either or both of the Luer parts 20, 30 can be configured instead as a slip or as a threaded lock Luer part. As shown, it will be apparent that the female Luer 30 is configured so that it may receive either an external male lock Luer or an external male slip Luer to make the fluid connection. Similarly, internal threads 29 are provided inside the skirt 28 of the male Luer part 20 so that it can be readily connected to either an external female lock Luer or an external female slip Luer.

The fluid flow passageway 24 in the male Luer part 20 extends longitudinally from the male extension part 26 to the seat 22. The female Luer part 30 shown in FIGS. 1–3 and 4–6, has an axially extending internal cavity 36 which may have an end portion 38 of non-circular configuration, for a purpose to be described.

Figure 16:
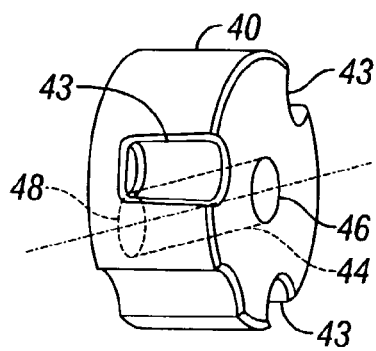
FIG. 16 is a perspective view of a seal.
Figure 17:
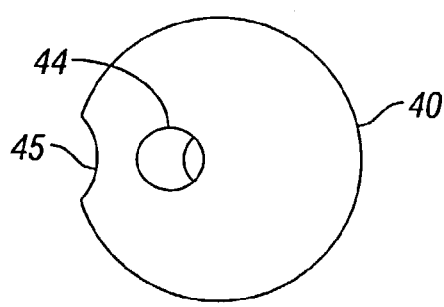
FIG. 17 is a left end view of the seal.
Figure 18:
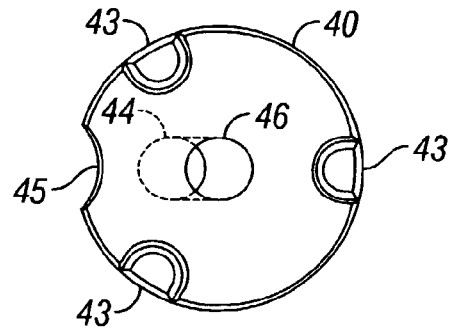
FIG. 18 is a right end view of the seal.

The seal 40 (see FIGS. 16–18) has a generally cylindrical shape with a fluid flow passageway 44 extending from an axially aligned end 46 in fluid communication with passage 24 to an off-center positioned end 48. The seal 40 is made of a firm but compressible elastomer, preferably silicone, the peripheral edge of which is preferably partially compressed between the seat 22 and the end wall 32 of the female Luer housing during assembly of the seal. The seal 40 has at least one and preferably three axially extending grooves 43 on its annular surface which mate with axially extending ribs 23 (FIG. 8) in the male Luer part 20 to non-rotatably position the seal 40 in the male Luer part 20. A longitudinally extending locating groove 45 is also provided on the annular surface of the seal 40 so that the seal 40 may be inserted into the male Luer part 20 along the finger 37.

A male end Luer contamination cap 50 which may be made of polyethylene plastic, may be provided for enclosing the extension 26 of the medical connector during shipment or when not in use.

Figure 10:
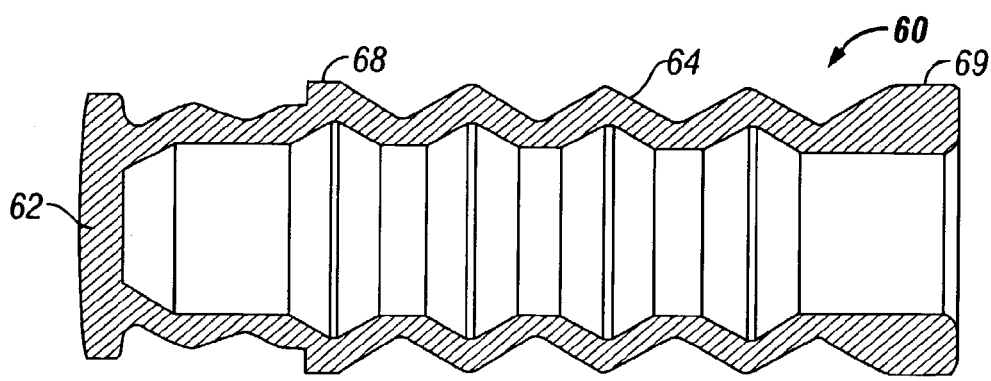
FIG. 10 is a cross-sectional elevation view of the swabbable stopper.
Figure 11:
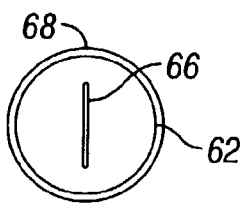
FIG. 11 is a left end view of the stopper.
Figure 12:
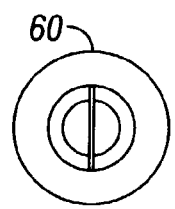
FIG. 12 is a right end view of the stopper.

As seen in FIGS. 10–12, a swabbable elastomeric stopper 60 having a normally closed end 62 and a depending corrugated skirt 64 is slidably mounted in the female Luer part 30 to normally close the open end thereof. A transversely extending slit 66 is provided through the normally closed end 62 of the elastomeric stopper 60 so that the slit can be opened when a male Luer end 102 of an external lock Luer 100 (FIG. 3A) engages the end 62 to push it over the end of a flow conducting insert 90 (to be described) when a flowline connection is made to the connector. It will be understood that the slit 66 may be a single transversely extending slit or two or more slits in form of a cross or any other functionally equivalent configuration such that the normally closed end 62 of the stopper 60 may be displaced as desired by the male Luer end 102 when a flowline connection is made. The stopper 60 also has an annular collar 68 which slidably engages the interior annular wall of the cavity 36 in the female Luer part 30 and a cylindrical end 69 which engages and seals off between the inside of the female Luer and the exterior of the insert 90 which also functions as a stopper guide.

Figure 13:
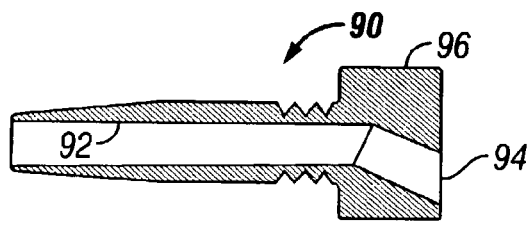
FIG. 13 is a cross-sectional elevation view of the flow conducting insert.
Figure 14:
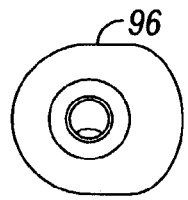
FIG. 14 is a left end view of the insert.
Figure 15:
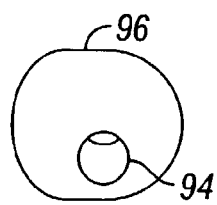
FIG. 15 is a right end view of the insert.

FIGS. 13–15 show the fluidic channel insert or fluid conducting insert 90, which may be made of polycarbonate, polypropylene, polyethylene or the like. The insert 90 may be integrally formed as shown or of multi-piece construction with a rigid or axially collapsible lumen having a central flow passageway 92. Axial collapsibility of the insert 90 is preferably provided by making the insert 90 of polypropylene or polyethylene with flexible corrugations 98 near the heel 96 of the insert 90. The corrugations 98 are not considered essential but, if provided, permit slight axial collapsibility of the insert 90 if contacted during activation by the end of an external male Luer 100. This avoids force transmission by the insert 90 and undesired deformation of the seal 40. Preferably the insert 90 is rounded at its left end as seen in the drawings for opening the slit 66 without damage. The flow passageway 92 axially extends from the left end of the insert 90 to an offset opening 94 in an end which provides a seat for the swabbable stopper 60, the seat being hereinafter referred to as a heel 96 due to its non-circular configuration shown in the drawings, at the other end of insert 90. The heel 96 is non-rotatably positioned in non-circular end portion 38 of the internal cavity 36 in the female Luer part 30 and is preferably restrained from axial sliding relative to the female Luer part 30 by an interference or press fit. Other complementary non-circular configurations of the heel 96 and end portion 38 can of course be chosen instead of the heel configuration depicted and those skilled in the art will appreciate that non-circular configurations, while preferred, are not essential.

Figure 3A:
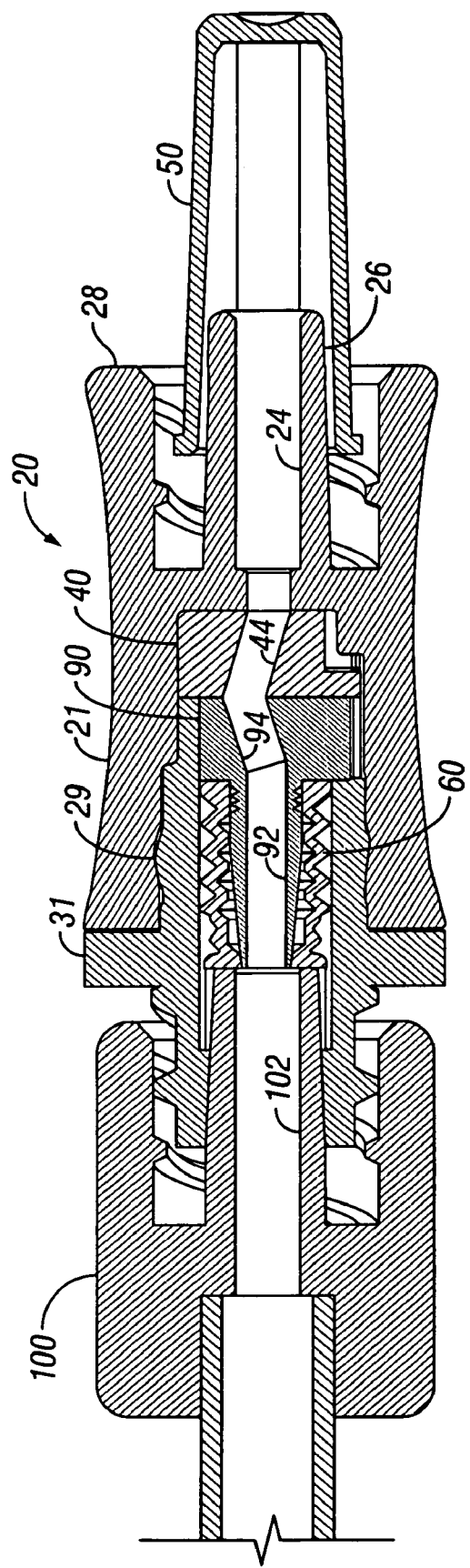
FIG. 3A is a view like FIG. 2A with the stopper end displaced from the FIG. 2A position by an external male Luer in a flowline and showing the connector in the open position.
Figure 3B:
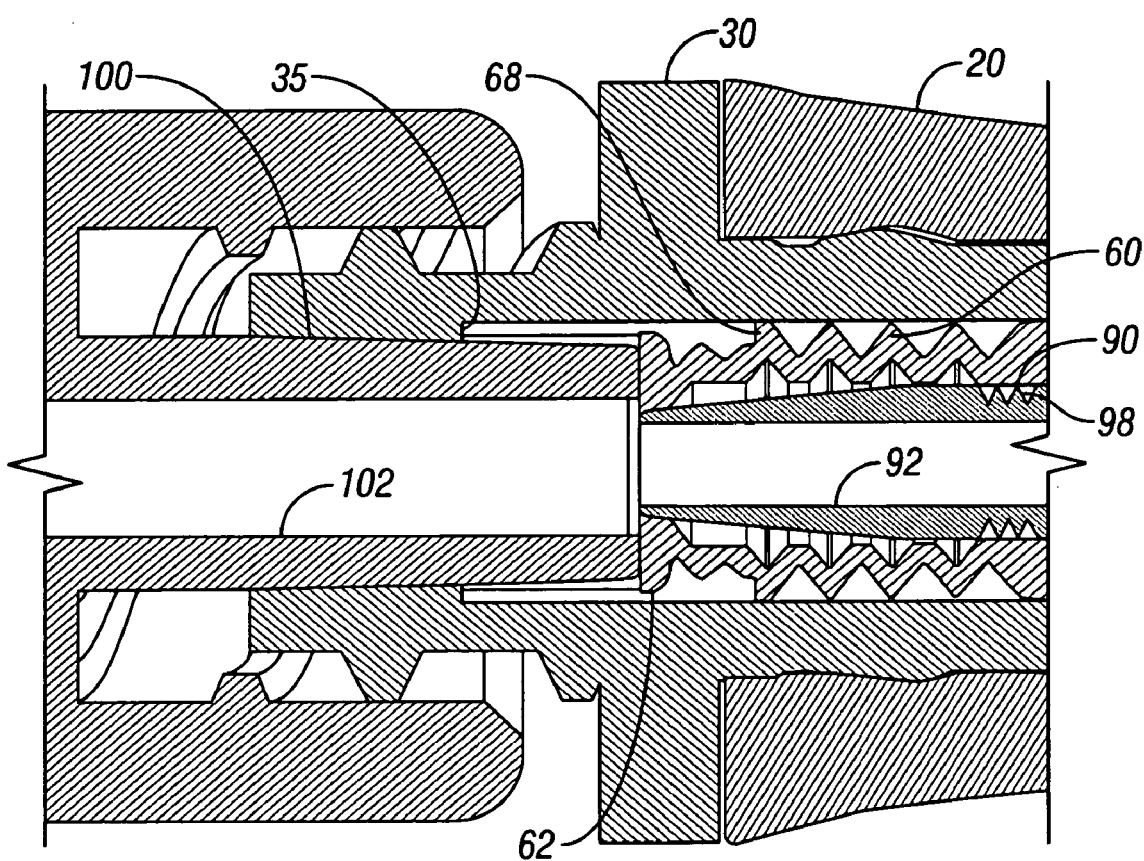
FIG. 3B is a portion of FIG. 3A to a substantially enlarged scale.
Figure 4:
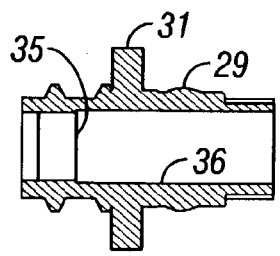
FIG. 4 is a cross-sectional elevation of a female Luer housing part.
Figure 5:
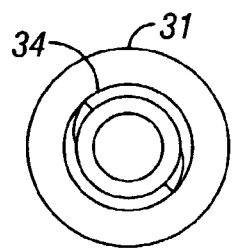
FIG. 5 is a left end view of the female Luer housing part.

Fluid flow is conducted through the connector from an external fluid flowline through the normally closed slit or slits 66 in the end wall 62 of the stopper which are displaced to the open position by engagement of the end wall 62 with an external male Luer 100, the end 102 of which pushes the end 62 of the stopper 60 to the right as best shown in the enlarged scale FIG. 3B so that the end of the insert 90 opens the slit or slits 66 allowing fluid flow axially through the flow passageway 92 in the insert 90 to the offset opening 94, then through the passageway 44 in the elastomeric valve element 40 to the passageway 24 in the male Luer extension 26.

Figure 2A:
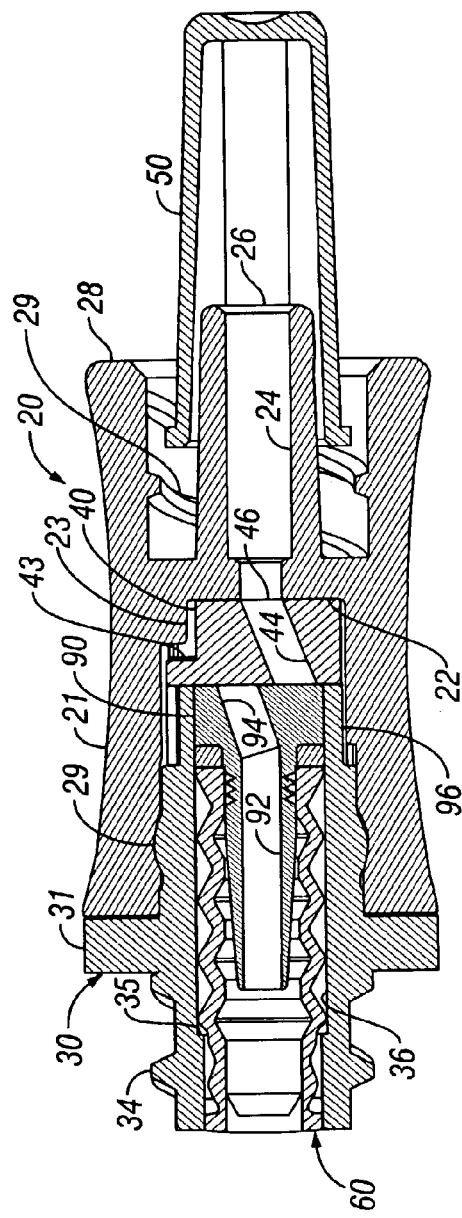
FIGS. 2A and 2b comprises a longitudinal cross-section views showing the medical connector of FIG. 1 with a swabbable stopper at the end of the female Luer part and with the connector in the closed position.
Figure 2B:
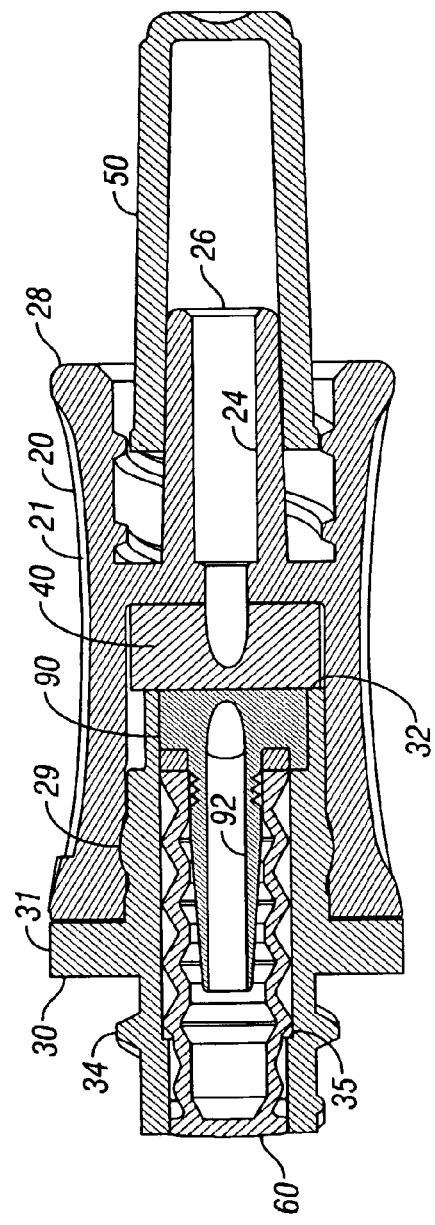

The resiliency and configuration of the skirt 64 of the swabbable stopper 60 are selected such that, during insertion of the external male Luer 100 into the female Luer part 30, the end 102 of an external male Luer 100 first engages the end wall 62 of the stopper which in turn is pushed over the rounded end of the insert 90 with the end wall 62 folding and compressing between the end 102 of the external male Luer and the insert 90 to prevent fluid entry into the annular space between the stopper 60 and the insert 90 as seen in FIG. 3A. Note that the end of the external male Luer 100 also engages the end 62 of the stopper 60 to prevent fluid leakage to annular space between the stopper 90 and interior wall of the female Luer part 30. The bellows portion of the skirt 64 between the collar 68 and the open end 69 of the skirt is compressed in the annular space between the inside wall of the female Luer part 30 and the outside wall of the insert 90 by engagement of at least some of the pleats of the bellows with the confining walls. It will be noted from viewing FIGS. 2A and 2B that the right end of the stopper 60 is also engaged with both the inside wall of the female Luer and the outside of the insert even when no flowline connection is made and when the end wall 62 of the stopper is flush with the end of the female Luer 30.

It will also be noted that the stopper collar 68 preferably axially engages an internally projecting stop shoulder 35 inside the female Luer part 30 with some axial compression of the stopper skirt 64 to provide a slight pre-load, and that the open end 64 of the skirt continuously engages and is resiliently seated against the heel 96 on the insert 90 to retain the swabbable stopper in position. Also, the stopper 60 can be retained in position in the female Luer in any other suitable fashion, for example by adhesive bonding to the heel 96 of the insert 90 in which instance the skirt collar 68 and abutting shoulder 35 in the female Luer are unnecessary.

Axial pressure which may be exerted on the insert 90 during connection by the external male Luer 100 may slightly move the insert to the right as seen in FIG. 3 if the insert 90 is slidably fitted into the female Luer. This may serve to further compress the seal 40 whose outer edge preferably has already been slightly compressed by the end wall 32 of the female Luer part 30 during assembly into the male Luer part 20. This compression of the seal may be avoided by use of the corrugations 98 on the insert 90 as described above. The Luer parts 20, 30 are preferably connected together by a snap fit provided by a mating annular groove and collar depicted at 29. The stopper skirt 64 may have what is described as a bellows or accordion like configuration as shown or it may be of sine wave or any other functionally equivalent configuration suitable for its intended purpose.

In the deactivated or closed position of the connector seen in FIGS. 2A and 2B, the bellows configuration of the skirt 64 of the stopper 60 urges the stopper end 62 outwardly of the female Luer part 30 so that the outer surface of the normally closed end 62 of the stopper 60 is substantially aligned or flush with the outer end of the female Luer part 30. This position is assured by provision of the skirt collar 68 and its engagement with the stop shoulder 35 in the female Luer part 30 at the positions shown. This permits easy swabbing of the stopper whenever the flowline is disconnected from the connector and prior to the making of a new connection thereto.

Needleless medical connectors constructed as above described eliminate exposure to diseases such as hepatitis and HIV caused by needle sticks and are suitable in various medical flow lines low pressure gravity drips as well as highly pressurized fluid flow lines due to the relatively straight fluid flow path through the connector which substantially eliminate sharp bends and other internal flow restrictions in the fluid flow passageways 92, 94, 44, 24. The connector can therefore be safely used for gravity blood transfusions without concern that pressurization induced by an infusion pump may degrade delicate blood cells.

All dead annular space between the female Luer part 30 and the swabbable stopper 60 and between the swabbable stopper and the lumen of the insert 90 is sealed from fluid entry by engagement of the walls of the stopper 60 and the adjacent parts. This feature results in minimization of potential infections resulting from solid and bacterial contaminants from fluid which may collect or stagnate in dead space as well as reduction in the amount of fluid, such as expensive medication, required to prime the connector prior to activation since only the internal passageways 92, 94 in the connector need be filled with priming fluid.

Negative pressure or bolus suck back upon disconnection of the external male Luer 100 is prevented simply by ensuring that the male and female Luer parts have been rotated to the Closed position prior to disconnection.

The connector may be made of clear plastic materials to enable visualization of the flow path and the parts may be readily injection molded and assembled without the use of ultrasonic welding or adhesives, swaging or additional fasteners of any kind.

While the foregoing constitutes a complete description of the invention, it will be appreciated by persons skilled in the art that changes and modifications of an obvious nature can be made from the illustrated embodiment and that such changes and modifications are considered within the scope of protection which is to be evaluated solely with respect to the attached claims.

The invention claimed is:

1. A medical connector having a longitudinal axis and interconnected axially aligned relatively rotatable male and female Luer parts forming a housing whereby relative rotation of said parts opens and closes a fluid flow path through said connector, said parts being configured for connection to external male and female Luer flowlines;

a flow conducting insert non-rotatably affixed in said female Luer part, said insert having an internal fluid passageway extending from a first axially aligned end to a second end, said second end being offset from said axis;

a compressible seal in said male Luer part, said seal abutting said second end of said insert and having a flow passageway extending between a first axially offset end at said second end of said insert to an axially aligned second end, such that said ends of said flow passageways in abutting ends of said insert and seal may be aligned to open said flow path; and an elastomeric stopper on said insert, said stopper having a swabbable end providing a deformable normally closed opening which may be opened by pushing said swabbable end over said insert by an external male Luer received in said female Luer part, said stopper having an annular axially collapsible skirt engaged with said female Luer part and said insert.

2. The medical connector of claim 1, wherein said first end of said insert is rounded to facilitate opening of said normally closed opening.

3. The medical connector of claim 2, wherein in said insert includes a seat engageable with said second end of said skirt.

4. The medical connector of claim 3, further comprising relatively engageable stop surfaces on said skirt and said female Luer part to axially retain said skirt in said female Luer part with an exterior surface of said end of said stopper flush with a surrounding portion of said female Luer part.

5. The medical connector of claim 4, wherein said skirt has an axially expansible and contractible portion between said annular seat and said stop surface.

6. The medical connector of claim 5, wherein said skirt slidably contacts said female Luer part and said insert.

7. The medical connector of claim 6, wherein said skirt includes a sealing portion which engages said female Luer part and said insert.

8. The medical connector of claim 1, wherein said female and male Luer parts have abutting faces and exposed surfaces adjacent said faces, said exposed surfaces having indicia which may be aligned at full open and closed positions of the connector.

9. The medical connector of claim 8, wherein said abutting faces extend in radial planes.

10. The medical connector of claim 8, further comprising slidably engageable surfaces on said female and male Luer parts defining full open and closed positions of said connector.

11. The medical connector of claim 1, wherein said female Luer part and said seal have abutting radially extending surfaces.

12. The medical connector of claim 11, wherein said insert and said seal have abutting radially extending surfaces.

13. The medical connector of claim 1, wherein said female and male Luer parts are connected by a snap fit.

14. The medical connector of claim 13, wherein said snap fit connection of said male and female Luer parts causes compression of a peripheral portion of said seal.

15. The medical connector of claim 1, wherein said insert and said female Luer part have mating portions of non-circular cross-section for non-rotatably positioning said insert in said female Luer part.

16. The medical connector of claim 1, wherein said seal and said male Luer part have at least one mating groove and rib to non-rotatably position said seal in said male Luer part.

17. The medical connector of claim 1, wherein said female and male Luer parts and said insert are made of polycarbonate and said stopper and said seal are made of silicone.

18. A medical connector having a longitudinal axis and interconnected axially aligned relatively rotatable male and female Luer parts forming a housing whereby relative rotation of said parts opens and closes a fluid flow path through said connector, said parts being configured for connection to external male and female Luer flowlines;

a flow conducting insert non-rotatably affixed in said female Luer part, said insert having an internal fluid passageway extending from a first axially aligned end to a second end, said second end being offset from said axis, said insert having an axially compressible section;

a compressible seal in said male Luer part, said seal abutting said second end of said insert and having a flow passageway extending between a first axially offset end at said second end of said insert to an axially aligned second end, such that said ends of said flow passageways in abutting ends of said insert and seal may be aligned to open said flow path; and an elastomeric stopper on said insert, said stopper having a swabbable end providing a deformable normally closed opening which may be opened by pushing said swabbable end over said insert by an external male Luer received in said female Luer part.

19. The medical connector of claim 18, wherein said axially compressible section of said insert is corrugated.

20. The medical connector of claim 19 wherein in said insert includes a seat engageable with said second end of said skirt.

21. The medical connector of claim 20, wherein said corrugated section is proximate said seat.

* * * * *